United States Patent [19]

Berg et al.

[11] Patent Number: 4,806,209

[45] Date of Patent: * Feb. 21, 1989

[54] SEPARATION OF FORMIC ACID FROM DIOXANE BY EXTRACTIVE DISTILLATION

[76] Inventors: Lloyd Berg; Rudolph J. Szabados, both of 1314 S. Third Ave., Bozeman, Mont. 59715

[*] Notice: The portion of the term of this patent subsequent to Jan. 31, 2006 has been disclaimed.

[21] Appl. No.: 185,419

[22] Filed: Apr. 25, 1988

[51] Int. Cl.[4] .................. B01D 3/40; C07C 51/44; C07D 319/12
[52] U.S. Cl. .............................. 203/51; 203/56; 203/57; 203/60; 203/61; 203/62; 203/63; 203/64; 203/65; 549/377; 562/609
[58] Field of Search ............ 203/57, 51, 61, 60, 203/62, 63, 64, 65, 56; 549/377; 562/609, 608

[56] References Cited

U.S. PATENT DOCUMENTS

| 2,954,392 | 9/1960 | Rylander | 568/410 |
| 4,007,095 | 2/1977 | Wolf et al. | 549/377 |
| 4,035,271 | 7/1977 | Nemtsov et al. | 204/182.4 |
| 4,285,881 | 8/1981 | Yang | 549/377 |

FOREIGN PATENT DOCUMENTS 55-85584  6/1980  Japan .................. 549/377

Primary Examiner—Wilbur Bascomb

[57] ABSTRACT

Dioxane cannot be completely removed from dioxane and formic acid mixtures by distillation because of the presence of the maximum azeotrope. Dioxane can be readily removed from dioxane - formic acid mixtures by extractive distillation in which the extractive agent is dimethylsulfoxide, either alone or admixed with certain high boiling organic compounds. Examples of effective agents are dimethylsulfoxide; DMSO and octanoic acid; DMSO, neodecanoic acid and methyl salicylate.

2 Claims, No Drawings

SEPARATION OF FORMIC ACID FROM DIOXANE BY EXTRACTIVE DISTILLATION

FIELD OF THE INVENTION

This invention relates to a method for separating formic acid from dioxane using certain higher boiling liquids as the agent in extractive distillation.

DESCRIPTION OF PRIOR ART

Extractive distillation is the method of separating close coiling compounds or azeotropes by carrying out the distillation in a multiplate rectification column in the presence of an added liquid or liquid mixture, said liquid(s) having a boiling point higher than the compounds being separated. The extractive agent is introduced near the top of the column and flows downward until it reaches the stillpot or reboiler. Its presence on each plate of the rectification column alters the relative volatility of the close boiling compoinds in a direction to make the separation on each plate greater and thus require either fewer plates to effect the same separation or make possible a greater degree of separation with the same number of plates. When the compounds to be separated normally form an azeotrope, the proper agents will cause them to boil separately during the extractive distillation and thus make possible a separation in a rectification column that cannot be done at all when no agent is present. The extractive agent should boil higher than any of the close boiling liquids being separated and not form minimum azeotropes with them. Usually the extractive agent is introduced a few plates from the top of the column to insure that none of the extractive agent is carried over with the lowest boiling component. This usually requires that the extractive agent boil twenty Centigrade degrees or more than the lowest boiling component.

At the bottom of a continuous column, the less volatile components of the close boiling mixtures and the extractive agent are continuously removed from the column. The usual methods of separation of these two components are the use of another rectification column, cooling and phase separation or solvent extraction.

Formic acid, B.P.=100.8° C., and dioxane, B.P.=101.4° C. form a maximum axeotrope boiling at 113.4° C. and containing 43 wt. % formic acid. When these two are found together in mixtures, either alone or with other liquids, distillation will only produce the azeotrope, never pure formic acid or dioxane. Thus any liquid mixture containing these two will on distillation produce the azeotrope. Extractive distillation would be an attractive method of effecting the separation of formic acid from dioxane if agents can be found that (1) will break the formic acid - dioxane azeotrope and (2) are easy to recover from the formic acid, that is, form no azetrope with formic acid and boil sufficiently above formic acid to make the separation by rectification possible with only a few theoretical plates.

Extractive distillation typically requires the addition of an equal amount to twice as much extractive agent as the acetic acid - diozane on each plate of the rectification column. The extractive agent should be heated to about the same temperature as the plate into which it is introduced. Thus extractive distillation imposes an additional heat requirement on the column as well as somewhat larger plates. However this is less than the increase occasioned by the additional agents required if the separation is done by azeotropic distillation. Another consideration in the selection of the extractive distillation agent is its recovery from the bottoms product. The usual method is by rectification in another column. In order to keep the cost of this operation to a minimum, an appreciable boiling point difference between the compound being separated and the extractive agent is desirable. It is desirable that the extractive agent be miscible with formic acid otherwise it will form a two-phase azeotrope with the formic acid in the recovery column and some other method of separation will have to be employed.

OBJECTIVE OF THE INVENTION

The object of this invention is to provide a process or method of extractive distillation that will enhance the relative volatility of dioxane to formic acid in their separation in a rectification column. It is a further object of this invention to identify suitable extractive distillation agents which will eliminate the dioxane - formic acid axeotrope and make possible the separation of dioxane from formic acid by rectification. It is a further object of this invention to identify organic compounds which are stable, can be separated from formic acid by rectification with relatively few plates and can be recycled to the extractive distillation column and reused with little decomposition.

SUMMARY OF THE INVENTION

The objects of the invention are provided by a process for separating dioxane from formic acid which entails the use of certain oxygenated or sulfur containing organic compounds as the agent in extractive distillation.

DETAILED DESCRIPTION OF THE INVENTION

We have discovered that dimethylsulfoxide (DMSO), either alone or admixed with other high boiling organic compounds, will effectively negate the dioxane - formic acid maximum azeotrope and permit the separation of dioxane from formic acid by rectification when employed as the agent in extractive distillation. Table 1 lists DMSO and its mixtures and the approximate proportions that we have found to be effective. The data in Table 1 was obtained in a vapor-liquid equilibrium still. In each case, the starting material was the dioxane-formic acid azeotrope.

TABLE 1

Extractive Distillation Agents Which Are Effective In Breaking The Formic Acid - Dioxane Azeotrope

| Compounds | Ratios | | Relative Volatility | |
|---|---|---|---|---|
| Dimethylsulfoxide (DMSO) | 1 | 6/5 | 10.9 | 11.9 |
| DMSO, Hexanoic acid | $(1/2)^2$ | $(3/5)^2$ | 2.7 | 6.8 |
| DMSO, Heptanoic acid | " | " | 6.8 | 2.8 |
| DMSO, Octanoic acid | " | " | 3.4 | 3.1 |
| DMSO, Pelargonic acid | " | " | 2.8 | 3.5 |
| DMSO, Neodecanoic acid | " | " | 4.0 | 3.0 |
| DMSO, Acetyl salicylic acid | " | " | 3.1 | 1.5 |
| DMSO, Adipic acid | " | " | 1.7 | 1.9 |
| DMSO, Azelaic acid | " | " | 2.1 | 3.2 |
| DMSO, Benzoic acid | " | " | 2.4 | 2.2 |
| DMSO, p-tert. Butyl benzoic acid | " | " | 1.7 | 1.7 |
| DMSO, Cinnamic acid | " | " | 2.3 | 2.7 |
| DMSO, Salicylic acid | " | " | 1.6 | 1.2 |
| DMSO, Glutaric acid | " | " | 2.3 | 1.5 |
| DMSO, Sebacic acid | " | " | 2.6 | 2.2 |
| DMSO, Itaconic acid | " | " | 1.1 | 1.2 |
| DMSO, o-Toluic acid | " | " | 1.8 | 2.1 |

TABLE 1-continued

Extractive Distillation Agents Which Are Effective In Breaking The Formic Acid - Dioxane Azeotrope

| Compounds | Ratios | | Relative Volatility | |
|---|---|---|---|---|
| DMSO, m-Toluic acid | " | " | 1.2 | 1.5 |
| DMSO, p-Toluic acid | " | " | 1.1 | 2.4 |
| DMSO, Malic acid | " | " | 2.0 | 2.3 |
| DMSO, Dodecanedioic acid | " | " | 2.8 | 2.3 |
| DMSO, p-Hydroxybenzoic acid | " | " | 1.1 | 1.4 |
| DMSO, 2-Benzoylbenzoic acid | " | " | 2.1 | 1.5 |
| DMSO, Hexanoic acid, Methyl benzoate | $(1/3)^3$ | $(2/5)^3$ | 2.7 | 6.8 |
| DMSO, Heptanoic acid, Ethyl benzoate | " | " | 3.6 | 2.7 |
| DMSO, Octanoic acid, Butyl benzoate | " | " | 3.1 | 3.1 |
| DMSO, Pelargonic acid, Benzyl benzoate | " | " | 5.1 | 3.3 |
| DMSO, Decanoic acid, Isophorone | " | " | 1.5 | 4.4 |
| DMSO, Neodecanoic acid, Methyl salicylate | " | " | 3.0 | 3.1 |
| DMSO, Acetyl salicylic acid, Cyclohexanone | " | " | 1.3 | 1.1 |
| DMSO, Adipic acid, Acetophenone | " | " | 1.9 | 1.8 |
| DMSO, Azelaic acid, Benzophenone | " | " | 1.7 | 1.9 |
| DMSO, Benzoic acid, Benzyl ether | " | " | 2.6 | 2.8 |
| DMSO, p-tert. Butyl benzoic acid, Butyl ether | " | " | 2.2 | 1.1 |
| DMSO, Cinnamic acid, Diethylene glycol dimethyl ether | " | " | 4.8 | 2.6 |
| DMSO, Salicylic acid, Diethylene glycol diethyl ether | " | " | 2.0 | 2.0 |
| DMSO, Glutaric acid, Adiponitrile | " | " | 1.4 | 2.1 |
| DMSO, Sebacic acid, Anisole | " | " | 1.1 | 1.7 |
| DMSO, Itaconic acid, Dipropylene glycol dibenzoate | " | " | 1.5 | 1.6 |
| DMSO, o-Toluic acid, Diethylene glycol dibenzoate | " | " | 1.8 | 1.2 |
| DMSO, m-Toluic acid, Ethylene glycol diacetate | " | " | 2.6 | 1.2 |
| DMSO, p-Toluic acid, Glycerol triacetate | " | " | 2.4 | 1.1 |
| DMSO, Malic acid, Glycerol triacetate | " | " | 2.6 | 1.5 |
| DMSO, Dodecanedioic acid, 2-Heptanone | " | " | 2.0 | 1.4 |
| DMSO, p-Hydroxybenzoic acid, Glycerol triacetate | " | " | 1.9 | 1.6 |
| DMSO, 2-Benzoylbenzoic acid, 2-Octanone | " | " | 1.7 | 1.3 |

TABLE 2

Data From Run Made In Rectification Column

| Agent | Column | Time | Weight % Dioxane | Weight % Formic acid | Relative Volatility |
|---|---|---|---|---|---|
| 33% DMSO, 33% Pelargonic acid, 33% Methyl benzoate | Overhead | ½ hr. | 97.3 | 2.7 | 2.7 |
| | Bottoms | | 28.8 | 71.2 | |
| | Overhead | 1 hr. | 98.9 | 1.1 | 2.9 |
| | Bottoms | | 45 | 55 | |
| | Overhead | 2 hr. | 99.1 | 0.9 | 3.6 |
| | Bottoms | | 25.4 | 74.6 | |

The ratios are the parts by weight of extractive agent used per part of dioxane - formic acid azeotrope. The relative volatilities are listed for each of the two ratios employed. The compounds which are effective when used in mixtures with DMSO are hexanoic acid, heptanoic acid, octanoic acid, pelargonic acid, decanoic acid, neodecanoic acid, benzoic acid, salicylic acid, cinnamic acid, o-toluic acid, m-toluic acid, p-toluic acid, p-hydroxybenzoic acid, p-tert. butyl benzoic acid, azelaic acid, isophorone, methyl benzoate, ethyl benzoate, acetyl salicylic acid, adipic acid, sebacic acid, itaconic acid, malic acid, dodecanedioic acid, 2-benzoylbenzoic acid, benzyl benzoate, methyl salicylate, cyclohexanone, benzophenone, butyl ether, diethylene glycol dimethyl ether, anisole, diethylene glycol dibenzoate, 2-heptanone, 2-octanone, butyl benzoate, acetophenone, benzyl ether, diethylene glycol diethyl ether, adiponitrile, dipropylene glycol dibenzoate, ethylene glycol diacetate, glycerol triacetate and glutaric acid.

The two relative volatilities shown in Table 1 correspond to the two different ratios investigated. For example, in Table 1, one part of DMSO mixed with one part of the dioxane - formic acid azeotrope gives a relative volatility of 10.9; with 6/5 parts of DMSO, the relative volatility is 11.9. One half part of DMSO mixed with one half part of octanoic acid with one part of the dioxane - formic acid azeotrope gives a relative volatility of 3.4; 3/5 parts of DMSO plus 3/5 parts of octanoic acid give 3.1. One third part of DMSO plus ⅓ part of octanoic acid plus ⅓ part of butyl benzoate with one part of the dioxane - formic acid azeotrope gives a relative volatility of 3.1; with 2/5 parts, these three give a relative volatility of 3.1. In every example in Table 1, the starting material is the dioxane - formic acid azeotrope which possesses a relative volatility of 1.00.

One of the mixtures, DMSO, pelargonic acid and methyl benzoate, listed in Table 1 and whose relative volatility had been determined in the vapor-liquid equilibrium still, was then evaluated in a glass perforated plate rectification column possessing 4.5 theoretical plates and the results listed in Table 2. The data in Table 2 was obtained in the following manner. The charge was 250 grams of the dioxane - formic acid azeotrope and after a half hour of operation in the 4.5 theoretical plate column to establish equilibrum, DMSO, pelargonic acid and methyl benzoate at 95° C. and 20 ml/min. was pumped in. The rectification was continued with sampling of the overhead and bottoms after two hours. The analysis is shown in Table 2 and was 99% dioxane, 0.9% formic acid in the overhead and 25.4% dioxane, 74.6% formic acid in the bottoms which gives a relative volatility of 3.6 of dioxane to formic acid. This indicates that the maximum azeotrope has been negated and separation accomplished. Without the extractive agent, the overhead would have been the maximum azeotrope composition of 57% dioxane. This proves that the extractive agent is negating the azeotrope and makes the rectification proceed as if the azeotrope no longer existed and brings out the more volatile dioxane, as overhead.

THE USEFULNESS OF THE INVENTION

The usefulness or utility of this invention can be demonstrated by referring to the data presented in Tables 1, 2. All of the successful extractive distillation agents show that dioxane and formic acid can be separated from their maximum azeotrope by means of distillation in a rectification column and that the ease of separation as measured by relative volatility is considerable. Without these extractive distillation agents, no improvement above the azeotrope composition will occur in the rectification column. The data also show that the most attractive agents will operate at a boilup rate low enough to make this a useful and efficient method of recovering high purity dioxane and formic acid from any mixture of these two including the maximum azeotrope. The stability of the compounds used and the boiling point difference is such that complete recovery and recycle is obtainable by a simple distillation and the amount required for make-up is small.

WORKING EXAMPLES

Example 1

Fifty grams of the dioxane - formic acid azeotrope and 50 grams of dimethylsulfoxide (DMSO) were charged to a vapor-liquid equilibrium still and refluxed for 11 hours. Analysis indicated a vapor composition of 80 % dioxane, 20 % formic acid, a liquid composition of 26.9% dioxane, 73.1 % formic acid which is a relative volatility of 10.9. Ten grams of DMSO were added and refluxing continued for another twelve hours. Analysis indicated a vapor composition of 79 % dioxane, 21 % formic acid, a liquid composition of 24.5 % dioxane, 75.5 % formic acid which is relative volatility of 11.9.

EXAMPLE 2

Fifty grams of the dioxane - formic acid azeotrope, 25 grams of DMSO and 25 grams of octanoic acid were charged to the vapor-liquid equilibrium still and reflexed for 12 hours. Analysis indicated a vapor composition of 56% dioxane, 44% formic acid and a liquid composition of 27% dioxane, 73 % formic acid which is a relative volatility of 3.4. Five grams of DMSO and five grams of octanoic acid were added and refluxing continued for another 12 hours. Analysis indicated a vapor composition of 60% dioxane, 40% formic acid and a liquid composition of 32% dioxane, 68% formic acid which is a relative volatility of 3.1.

EXAMPLE 3

Fifty grams of dioxane - formic acid azeotrope, 17 grams of DMSO, 17 grams of neodecanoic acid and 17 grams of methyl salicylate were charged to the vapor-liquid equilibrium still and refluxed for 16 hours. Analysis indicated a vapor composition of 52.9% dioxane, 47.1% formic acid and a liquid composition of 26.4% dioxane, 73.6% formic acid which is a relative volatility of 3.1. Three grams each of DMSO, neodecanoic acid and methyl salicylate were added and refluxing continued for another eight hours. Analysis indicated a vapor compostion of 53.1% dioxane, 46.9% formic acid and a liquid composition of 27 % dioxane, 73 % formic acid which is a relative volatility of 3.1.

EXAMPLE 4

A glass perforated plate rectification column was calibrated with ethylbenzene and p-xylene which possesses a relative volatility of 1.06 and found to have 4.5 theoretical plates. A solution comprising 250 grams of the dioxane - formic acid azeotrope was placed in the stillpot and heated. When refluxing began, an extractive agent comprising 33% DMSO, 33% pelargonic acid and 33% methyl benzoate was pumped into the column at a rate of 20 ml/min. The temperature of the extractive agent as it entered the column was 95° C. After establishing the feed rate of the extractive agent, the heat input of the dioxane and formic acid in the stillpot was adjusted to give a total reflux rate of 10-20 ml/min. After one-half hour of operation, the overhead and bottoms samples of approximately two ml. were collected and analysed by gas chromatography. The overhead analysis was 97.3% dioxane, 2.7% formic acid. The bottoms analysis was 28.8% dioxane, 71.2% formic acid. Using these compositions in the Fenske equation, with the number of theoretical plates in the column being 4.5, gave an average relative volatility of 2.7 for each theoretical plate.

After one hour of continuous operation, the overhead analysis was 98.9% dioxane, 2.7% formic acid; the bottoms analysis was 45% dioxane, 55% formic acid which is a relative volatility of 2.9. After two hours of continuous operation, the overhead analysis was 99.1% dioxane, 0.9% formic acid; the bottoms analysis was 25.4% dioxane, 74.6% formic acid which is a relative volatility of 3.6.

We claim:

1. A method for recovering dioxane from mixtures of dioxane and formic acid which comprises distilling a mixture of dioxane and formic acid in a rectification column if the presence of about one part of an extractive agent per part of dioxane - formic acid mixture, recovering dioxane as overhead product and obtaining the formic acid and the extractive agent from the stillpot, wherein said extractive agent comprises dimethylsulfoxide.

2. The method of claim 1 in which the extractive agent comprises dimethylsulfoxide and at least one member from the group consisting of hexanoic acid, heptanoic acid, octanoic acid, pelargonic acid, decanoic acid, neodecanoic acid, acetyl salicylic acid, adipic acid, azelaic acid, benzoic acid, p-tert. butyl benzoic acid, cinnamic acid, salicylic acid, glutaric acid, sebacic acid, itaconic acid, o-toluic acid, m-toluic acid, p-toluic acid, malic acid, dodecanedioic acid, p-hydoxybenzoic acid, 2-benzoyl benzoic acid, methyl benzoate, ethyl benzoate, butyl benzoate, benzyl benzoate, isophorone, methyl salicylate, cyclohexanone, acetophenojne, benzophenone, benzyl ether, butyl ether, diethylene glycol dimethyl ether, diethylene glycol diethyl eiither, adiponitrile, anisole, dipropylene glycol dibenzoate, diethylene glycol dibenzoate, ethylene glycol diacetate, glycerol triacetate, 2-heptanone and 2-octanone.

* * * * *